(12) United States Patent
Tsaur

(10) Patent No.: US 6,779,938 B1
(45) Date of Patent: Aug. 24, 2004

(54) CONTAINER WITH APPLICATOR

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 0 days.

(21) Appl. No.: 10/420,271

(22) Filed: Apr. 22, 2003

(51) Int. Cl.$^7$ ................................. B43K 5/11
(52) U.S. Cl. ........................ 401/132; 604/3; 206/210
(58) Field of Search ................. 401/132–137; 604/1–3; 206/209, 210, 361

(56) References Cited

U.S. PATENT DOCUMENTS

| | | | | |
|---|---|---|---|---|
| 3,958,571 A | * | 5/1976 | Bennington | 604/3 |
| 4,175,008 A | * | 11/1979 | White | 600/572 |
| 4,206,843 A | * | 6/1980 | Rainey | 206/216 |
| 4,312,950 A | * | 1/1982 | Snyder et al. | 600/572 |
| 4,492,305 A | * | 1/1985 | Avery | 206/210 |
| 4,740,194 A | * | 4/1988 | Barabino et al. | 604/3 |
| 4,875,602 A | * | 10/1989 | Chickering et al. | 222/187 |
| 5,078,968 A | * | 1/1992 | Nason | 422/58 |

* cited by examiner

*Primary Examiner*—Gregory L. Huson
*Assistant Examiner*—Huyen Le
(74) *Attorney, Agent, or Firm*—Joe Nieh

(57) ABSTRACT

A small slender sealed container with a built-in applicator that may be used to store small quantity of substance, such as medications, in a sealed environment and easily and sanitarily dispenses the fluid for application as desired is disclosed. The container with applicator comprises of a small slender container with a first end and a second end with a sealed compartment near the first end with an opening means for access to the contents in the sealed compartment between the first and second ends of the slender container and an applicator at the second end. When the sealed compartment near the first end is opened through the opening means, it is separated from the applicator at the second end. The applicator may then be used to retrieve the contents of the sealed compartment and apply the contents to the desired location.

20 Claims, 1 Drawing Sheet

CONTAINER WITH APPLICATOR

BACKGROUND

1. Field of Invention

The present invention relates to a small sealed container with an applicator. More specifically, the present invention relates to a small slender sealed container with a built-in applicator such as a cotton swab.

BACKGROUND

2. Description of Related Art

Small containers in the general form of an elongated tube are generally used to distribute and/or apply small quantities of products such as perfume, alcohol, and medications. The small container's contents are generally not exhausted with just one use. Therefore, the container must be re-closable or else the remaining contents must be disposed of.

Often, an applicator is required to retrieve and accurately apply the content of the container to the desired location. The applicator is generally a separate component that is inserted into the container to retrieve the content and then applied to the desired location. Some applicators are incorporated into the cap of the container such that when the cap is removed, the applicator is exposed and can be used to retrieve and apply the content of the container. Other applicators are completely separate from the container such that it is not a component of the container. With either design, the contents of the container risks contamination once it is opened. If contamination is a concern, a disposable applicator must be used each time the content is accessed.

With the existing designs, the containers are generally designed for multiple uses and, if contamination is a concern, a disposable applicator is required. Furthermore, the existing designs are generally bulkier and cost more to manufacture than the invention disclosed due to their unnecessarily large capacity and the multiple applicators required for multiple access to the content if contamination of the content is a concern. The existing designs are also more difficult to transport and store compactly.

SUMMARY OF THE INVENTION

The present invention is a small slender sealed container with a built-in applicator that may be used to store small quantity of substance, such as medications, in a sealed environment and easily and sanitarily dispenses the fluid for application as desired. The content of the slender container is completely sealed and will not leak or evaporate from the container and cannot be contaminated. The container with applicator comprises of a small slender container with a first end and a second end with a sealed compartment near the first end with an opening means for access to the contents in the sealed compartment between the first and second ends of the slender container and an applicator at the second end. When the sealed compartment near the first end is opened through the opening means, it is separated from the applicator at the second end. The applicator may then be used to retrieve the contents of the sealed compartment and apply the contents to the desired location. After application, the sealed compartment and the applicator are disposed of.

DETAILED DESCRIPTION OF THE PREFERRED EMBODIMENT

Figure 1:
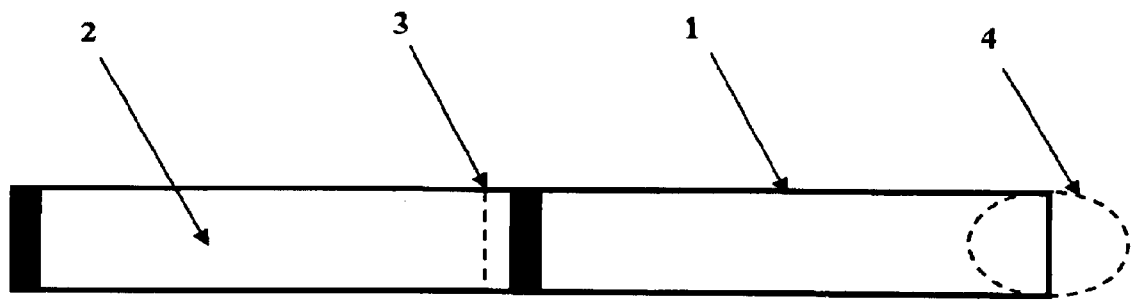
FIG. 1 shows the preferred embodiment of the container with applicator.

FIG. 1 shows the preferred embodiment of the container with applicator. The preferred embodiment of the container with applicator comprises an elongated housing 1 with a first end and a second end. A sealed compartment 2 is located near the first end with an opening means 3 between the first end and the second end of the elongated housing 1. An applicator 4 is affixed to the second end. The container with applicator may be used to store and dispense small amount of substance in the sealed compartment 2 by opening the sealed compartment 2 through the opening means 3 and separating the now opened sealed compartment 2 from the first end with the applicator 4 thereby exposing the contents in the sealed compartment 2 to be accessed by the applicator 4 through the resulting opening in the sealed compartment 2.

Figure 2:
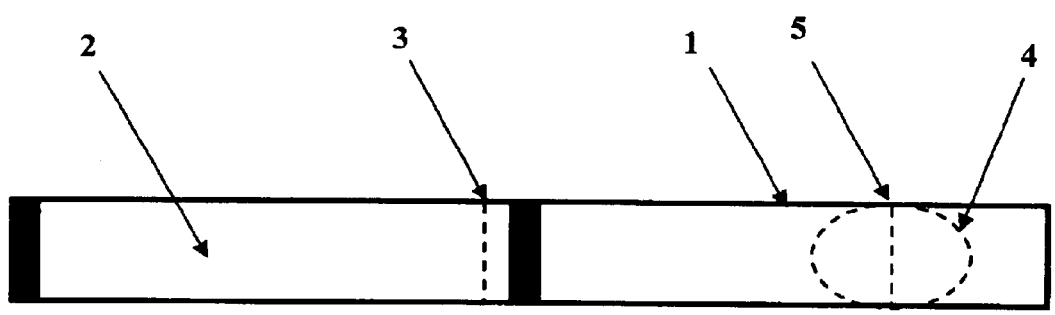
FIG. 2 shows another embodiment of the container with applicator.

FIG. 2 shows another embodiment of the container with applicator. In this embodiment, the container with applicator comprises an elongated housing 1 with a first end and a second end. A sealed compartment 2 is located near the first end with an opening means 3 between the first end and the second end of the elongated housing 1. An applicator 4 is affixed within the elongated housing 1 between the second end and the sealed compartment 2. A second opening means 5 in the form of a score line that allows the elongated housing 1 to break open at the score line is located at the location of the applicator 4 such that when the elongated housing 1 is broken open at the second opening means 5 the applicator 4 is exposed. The container with applicator may be used to store and dispense small amount of substance in the sealed compartment 2 by exposing the applicator 4 with the second opening means 5 and opening the sealed compartment 2 through the opening means 3 and separating the now opened sealed compartment 2 from the first end with the applicator 4 thereby exposing the contents in the sealed compartment 2 to be accessed by the applicator 4 through the resulting opening in the sealed compartment 2.

Figure 3:
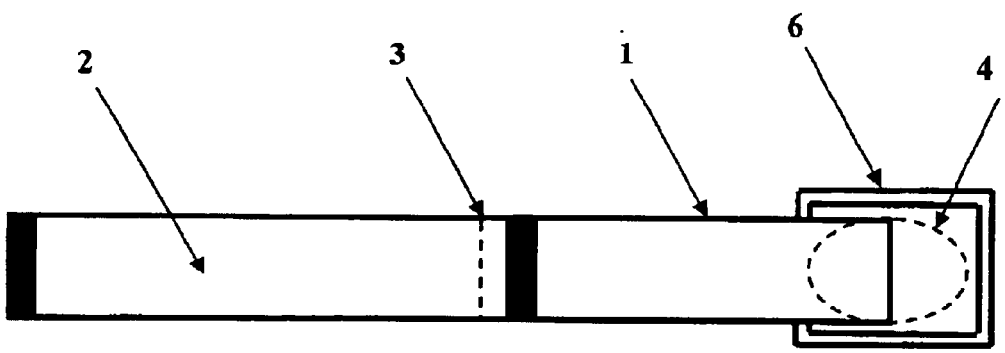
FIG. 3 shows another embodiment of the container with applicator.

FIG. 3 shows yet another embodiment of the container with applicator. In this embodiment, the container with applicator comprises an elongated housing 1 with a first end and a second end. A sealed compartment 2 is located near the first end with an opening means 3 between the first end and the second end of the elongated housing 1. An applicator 4 is affixed to the second end. The applicator 4 is protected with a removable cover 6 such as a cap. The container with applicator may be used to store and dispense small amount of substance in the sealed compartment 2 by removing the removable cover 6 thereby exposing the applicator 4 and opening the sealed compartment 2 through the opening means 3 and separating the now opened sealed compartment 2 from the first end with the applicator 4 thereby exposing the contents in the sealed compartment 2 to be accessed by the applicator 4 through the resulting opening in the sealed compartment 2.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A container with applicator comprising a one-piece elongated housing with generally a constant diameter throughout its length with a first end and a second end with a sealed compartment near the first end with an opening means between the first end and the second end and an applicator affixed to the second end wherein the one-piece elongated housing may be used to store and dispense small amount of substance by opening the sealed compartment through the opening means and separating the now opened sealed compartment from the second end with the applicator thereby exposing the contents in the sealed compartment to be accessed by the applicator through the resulting opening in the sealed compartment.

2. A container with applicator as in claim 1, wherein the opening means is a scoring that can be broken open to release the substance in the sealed compartment.

3. A container with applicator as in claim 2, wherein the applicator is a brush.

4. A container with applicator as in claim 2, wherein the applicator is a ball of cotton.

5. A container with applicator as in claim 2, wherein the applicator is a sponge.

6. A container with applicator as in claim 1, wherein the substance is a liquid.

7. A container with applicator as in claim 1, wherein the substance is a powder.

8. A container with applicator as in claim 1, wherein the applicator is a brush.

9. A container with applicator as in claim 1, wherein the applicator is a ball of cotton.

10. A container with applicator as in claim 1, wherein the applicator is a sponge.

11. A container with applicator comprising a one-piece elongated housing with generally a constant diameter throughout its length with a first end and a second end with a sealed compartment near the first end with an opening means between the first end and the second end and an applicator affixed to the second end with a removable cover covering said applicator wherein the one-piece elongated housing may be used to store and dispense small amount of substance by opening the sealed compartment through the opening means and separating the now opened sealed compartment from the second end with the applicator thereby exposing the contents in the sealed compartment to be accessed by the applicator through the resulting opening in the sealed compartment after removing the removable cover from the applicator.

12. A container with applicator as in claim 11, wherein the opening means is a scoring that can be broken open to release the substance in the sealed compartment.

13. A container with applicator as in claim 12, wherein the applicator is a brush.

14. A container with applicator as in claim 12, wherein the applicator is a ball of cotton.

15. A container with applicator as in claim 12, wherein the applicator is a sponge.

16. A container with applicator as in claim 11, wherein the substance is a liquid.

17. A container with applicator as in claim 11, wherein the substance is a powder.

18. A container with applicator as in claim 11, wherein the applicator is a brush.

19. A container with applicator as in claim 11, wherein the applicator is a ball of cotton.

20. A container with applicator as in claim 11, wherein the applicator is a sponge.

\* \* \* \* \*